(12) United States Patent  
Sjöman et al.

(10) Patent No.: US 9,131,310 B2  
(45) Date of Patent: Sep. 8, 2015

(54) HEARING PROTECTOR

(75) Inventors: Henrik J. Sjöman, Skillingaryd (SE); Johan Håkansson, Växjö (SE)

(73) Assignee: 3M Innovative Properties Company, St. Paul, MN (US)

( * ) Notice: Subject to any disclaimer, the term of this patent is extended or adjusted under 35 U.S.C. 154(b) by 636 days.

(21) Appl. No.: 12/992,075

(22) PCT Filed: Apr. 27, 2009

(86) PCT No.: PCT/SE2009/000214  
§ 371 (c)(1),  
(2), (4) Date: Nov. 10, 2010

(87) PCT Pub. No.: WO2009/139682  
PCT Pub. Date: Nov. 19, 2009

(65) Prior Publication Data  
US 2011/0064239 A1 Mar. 17, 2011

(30) Foreign Application Priority Data  
May 12, 2008 (SE) ...................... 0801067

(51) Int. Cl.  
*A61F 11/06* (2006.01)  
*H04R 1/10* (2006.01)  
(Continued)

(52) U.S. Cl.  
CPC .............. *H04R 1/1075* (2013.01); *A61F 11/14* (2013.01); *H04R 1/1083* (2013.01); *A61F 2011/145* (2013.01); *H04R 5/033* (2013.01)

(58) Field of Classification Search  
CPC . A61F 11/14; A61F 2011/145; H04R 1/1075; H04R 1/1083; H04R 5/033  
USPC ............ 381/72, 74, 370–375, 322, 323, 345, 381/346, 350, 351, 71; 379/430–432  
See application file for complete search history.

(56) References Cited

U.S. PATENT DOCUMENTS 2,235,372 A 3/1941 Kalbitz  
3,087,028 A 4/1963 Bonnin  
(Continued)

FOREIGN PATENT DOCUMENTS

CN 101166488 4/2008  
DE 9012732 12/1990  
(Continued)

OTHER PUBLICATIONS

European Application 09746842 Supplementary European Search Report dated Oct. 29, 2013.

*Primary Examiner* — Lun-See Lao  
(74) *Attorney, Agent, or Firm* — Melanie G. Gover

(57) ABSTRACT

A hearing protector has two closed muffs (2) which sealingly abut against the wearer's head, so that there is formed a closed space in each muff (2) and about the user's ear. A loudspeaker (4) is disposed interiorly in the muff and has a membrane (5) whose one side is turned to face towards the user's ear, and whose opposing side is turned to face towards a closed volume which is defined by the membrane and an enclosure. In order to improve the base reproduction in listening to music, the interior of the enclosure is, via at least one hole or one duct, in communication with the ambient surroundings outside the closed space of the muff (2). In one preferred embodiment, the enclosure comprises a capsule (7) which is integrated part of the loudspeaker (4).

11 Claims, 2 Drawing Sheets

(51) Int. Cl.
*A61F 11/14* (2006.01)
*H04R 5/033* (2006.01)

(56) References Cited

U.S. PATENT DOCUMENTS

| | | |
|---|---|---|
| 3,306,991 A | 2/1967 | Wood |
| 3,394,226 A | 7/1968 | Andrews, Jr. |
| 3,456,263 A | 7/1969 | Aileo |
| 3,579,640 A | 5/1971 | Beguin |
| 3,833,939 A | 9/1974 | Dostourian |
| 3,869,584 A | 3/1975 | Wilde |
| 3,890,474 A | 6/1975 | Glicksberg |
| 3,952,158 A | 4/1976 | Kyle et al. |
| 4,027,113 A | 5/1977 | Matsumoto |
| 4,064,362 A | 12/1977 | Williams |
| 4,066,849 A | 1/1978 | Chladil, Sr. |
| 4,087,653 A | 5/1978 | Frieder, Jr. et al. |
| 4,302,635 A | 11/1981 | Jacobsen |
| 4,327,257 A | 4/1982 | Schwartz |
| 4,829,571 A | 5/1989 | Kakiuchi et al. |
| 4,833,719 A | 5/1989 | Carme et al. |
| 4,867,149 A | 9/1989 | Falco |
| 4,928,311 A | 5/1990 | Trompler |
| 4,965,836 A | 10/1990 | Andre |
| 4,985,925 A | 1/1991 | Langberg et al. |
| 5,125,032 A | 6/1992 | Meister et al. |
| 5,181,252 A | 1/1993 | Sapiejewski |
| 5,251,263 A | 10/1993 | Andrea et al. |
| 5,402,497 A * | 3/1995 | Nishimoto et al. ............. 381/95 |
| 5,497,427 A | 3/1996 | Nageno |
| 5,519,783 A | 5/1996 | Kumar |
| 5,550,923 A * | 8/1996 | Hotvet ............................. 381/72 |
| 5,631,965 A | 5/1997 | Chang et al. |
| 5,675,658 A | 10/1997 | Brittain |
| 5,844,998 A | 12/1998 | Nageno |
| 6,118,878 A | 9/2000 | Jones |
| 6,631,279 B2 | 10/2003 | Rivera |
| 6,704,428 B1 | 3/2004 | Wurtz |
| 6,724,906 B2 | 4/2004 | Naksen |
| 6,728,388 B1 | 4/2004 | Nageno |
| 6,748,087 B1 | 6/2004 | Jones |
| 6,801,629 B2 | 10/2004 | Brimhall |
| 6,965,681 B2 | 11/2005 | Almqvist |
| 6,970,571 B2 | 11/2005 | Knorr |
| 7,099,485 B2 | 8/2006 | Dittli |
| 7,245,735 B2 | 7/2007 | Han |
| 7,308,106 B2 | 12/2007 | Vaudrey |
| 7,327,850 B2 | 2/2008 | Crump |
| 7,391,878 B2 | 6/2008 | Liao |
| 7,664,282 B2 | 2/2010 | Urso |
| 8,111,858 B2 | 2/2012 | Sapiejewski |
| 8,130,970 B2 | 3/2012 | Heringslack |
| 2001/0046304 A1 | 11/2001 | Rast |
| 2002/0001391 A1 | 1/2002 | Darbut |
| 2002/0003889 A1 | 1/2002 | Fischer |
| 2002/0080979 A1 | 6/2002 | Brimhall et al. |
| 2002/0080987 A1 | 6/2002 | Almqvist |
| 2003/0223612 A1 | 12/2003 | Knorr et al. |
| 2004/0125976 A1 | 7/2004 | Reneker |
| 2004/0125977 A1 | 7/2004 | Hong |
| 2004/0258253 A1 | 12/2004 | Wurtz |
| 2005/0013447 A1 | 1/2005 | Crump et al. |
| 2005/0220318 A1 | 10/2005 | Han |
| 2005/0254665 A1 | 11/2005 | Vaudrey et al. |
| 2006/0269090 A1 | 11/2006 | Sapiejewski |
| 2007/0044205 A1 | 3/2007 | Sato et al. |
| 2007/0183606 A1 | 8/2007 | Doty |
| 2007/0274529 A1 | 11/2007 | Nordin et al. |
| 2008/0011084 A1 | 1/2008 | Von Dach et al. |
| 2008/0192973 A1 | 8/2008 | Heringslack |
| 2008/0279411 A1 | 11/2008 | Suzuki |
| 2011/0124300 A1 | 5/2011 | Sinai |
| 2012/0177215 A1 * | 7/2012 | Bose et al. ....................... 381/74 |

FOREIGN PATENT DOCUMENTS

| | | | |
|---|---|---|---|
| DE | 10117704 | 6/2001 | |
| EP | 0465971 A2 | 1/1992 | |
| EP | 873040 | 10/1998 | |
| EP | 0967592 | 12/1999 | |
| EP | 0967592 A2 * | 12/1999 | ........... G10K 11/178 |
| EP | 1629808 A1 | 3/2006 | |
| EP | 1068771 B1 | 11/2008 | |
| FR | 2695302 | 3/1994 | |
| GB | 1160431 A | 8/1969 | |
| GB | 1289993 A | 9/1972 | |
| GB | 2445984 A | 7/2008 | |
| JP | S54-124532 U | 9/1979 | |
| JP | 3-274997 | 12/1991 | |
| JP | 7-170589 | 7/1995 | |
| WO | 87/04065 | 7/1987 | |
| WO | 91/07153 | 5/1991 | |
| WO | 95/00946 | 1/1995 | |
| WO | 96/08004 | 3/1996 | |
| WO | 97/28742 A1 | 8/1997 | |
| WO | 02/17838 | 3/2002 | |
| WO | 03/086124 | 10/2003 | |
| WO | 2005/051255 | 6/2005 | |
| WO | 2006/058319 | 6/2006 | |
| WO | 2006/118514 | 11/2006 | |
| WO | WO 2006118514 A1 * | 11/2006 | ............... H04R 1/10 |
| WO | 2008/099137 | 8/2008 | |
| WO | 2008/113822 | 9/2008 | |

* cited by examiner

HEARING PROTECTOR

CROSS REFERENCE TO RELATED APPLICATIONS

This application is a national stage filing under 35 U.S.C. 371 of PCT/SE2009/000214, filed Apr. 27, 2009, which claims priority to Swedish Application No. 0801067-0, filed May 12, 2008, the disclosure of which is incorporated by reference in its/their entirety herein.

TECHNICAL FIELD

The present invention relates to a hearing protector with loudspeakers and comprising a closed muff disposed at each ear of a user, the muff sealingly abutting against the user's head, whereby there is formed an enclosed space in the muff and around the user's ear, one loudspeaker disposed in at least one of the muffs and displaying a membrane whose one side is turned to face towards the ear of the user and whose opposing side is turned to face towards a closed volume which is defined by the membrane and an enclosure, and a drive unit for driving the loudspeaker.

BACKGROUND ART

Hearing protectors of the type mentioned way of introduction are previously known in the art in a multiplicity of different variations and are employed in noisy environments in order to protect the hearing of the user. The hearing protector is as a rule provided with a passive noise absorbent inside the muffs which are included in the hearing protector. The volume of the muffs and the nature of the noise absorbent may be adapted in response to the nature of the noise from which the user is to be protected.

The loudspeakers disposed in the hearing protectors may be a part of a communications system, may be connected to an installation for music reproduction, but may also be connected to a microphone located outside the hearing protectors in order to convey to the user ambient sound such as speech, and instructions from a person in the proximity, or also warning signals.

As regards oral comprehension, the prior art hearing protectors of this type are often fully sufficient, since the frequency path within that range which encompasses the majority of human speech is sufficiently good.

The loudspeaker element that is traditionally employed in these practical applications may have a diameter of the order of magnitude of 20 to 30 mm. In order to avoid acoustic shorting of the loudspeaker element, it is necessary to enclose the rear side of the loudspeaker element in a capsule which prevents pressure equalisation between both sides of the membrane. However, the volume in this capsule is so slight that the frequency path, or sound pressure curve, in the base range, i.e. frequencies of below approx. 300H, is negatively affected. In listening to music, this is a major shortcoming, which is particularly manifest when listening to popular music, since a base lift is often desirable in such circumstances.

Problem Structure

The present invention has for its object to design the hearing protector disclosed by way of introduction such that it will have an improved frequency path in the base range and, in particular in relation to the prior art technology, a lift in the frequency range of 20 to 300 Hz. The present invention also has for its object to design the hearing protector so that the sought-for improvements may be realised at low cost and with a marginal deterioration in damping.

Solution

The objects forming the basis of the present invention will be attained if the hearing protector disclosed by way of introduction is characterised in that the interior of the enclosure is, via at least one hole or duct, in communication with the ambient surroundings outside the closed space of the muff.

BRIEF DESCRIPTION OF TILE ACCOMPANYING DRAWINGS

The present invention will now be described in greater detail hereinbelow, with reference to the accompanying Drawings and Diagrams. In the accompanying Drawings.

Table 1 shows the frequency path in a relatively small muff, on the one hand according to the prior art technology and on the other hand in a number of variations of the present invention; and Table 2 shows the frequency path in a relatively large muff in analogy with the frequency path according to Table 1.

DESCRIPTION OF PREFERRED EMBODIMENT

Figure 1:
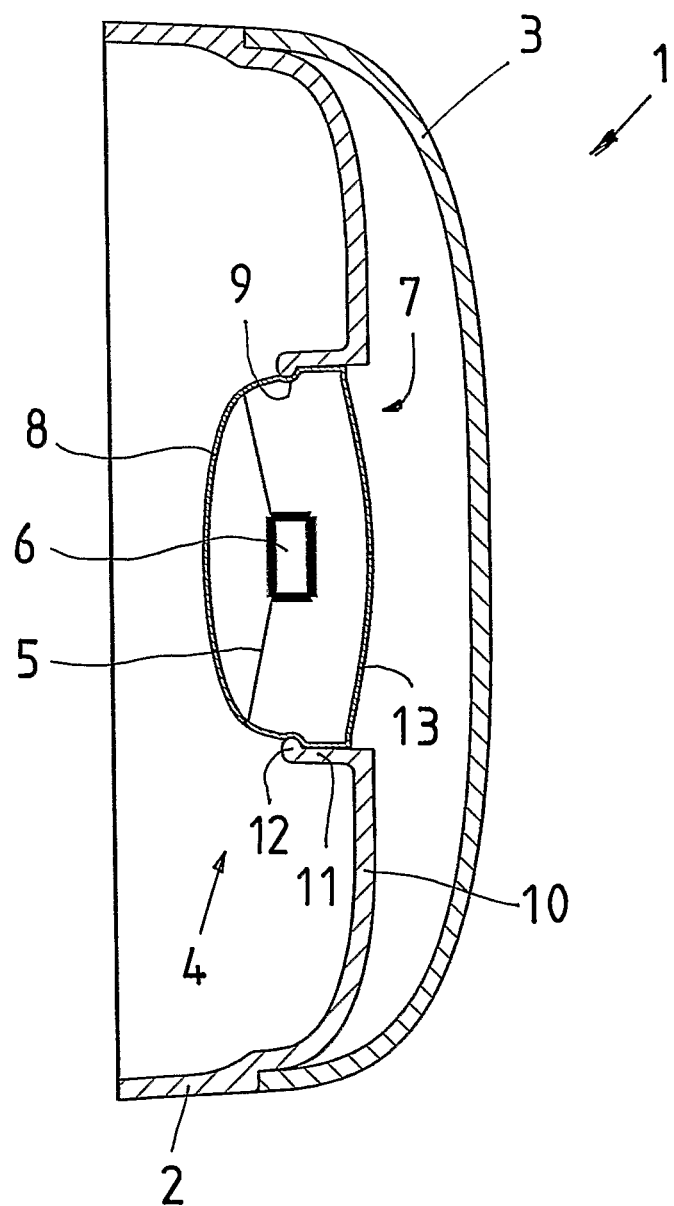
FIG. 1 is a simplified cross section through a first embodiment of a muff included in a protector according to the present invention.

Referring to the Drawings, FIG. 1 is a vertical cross section through a muff 1 included in the hearing protector according to the present invention. Normally, use is made of two muffs, one for each ear of the user, the muffs being interconnected by means of a resilient or flexible crown connection strap or by other means so that the muffs remain in position on and are urged with suitable force against the head of the user. The muffs may possibly also be integrated in a safety helmet. The muff 1 includes a muff section 2 and a covering section 3. The muff section 2 has, along its periphery, a sealing ring (not shown on the Drawings), which is intended to resiliently and sealingly abut against the user's head, around the ears. This implies that the muff section 2, the sealing ring and the user's head define a closed volume in which the user's ears are located.

The covering section 3 need not be tightly sealed against the ambient surroundings, but is merely intended for accommodating electronics, radio receiver, current source and the like, which are required for driving the loudspeaker element 4 interiorly disposed in the closed volume in the muff section 2. The loudspeaker element for use in the hearing protector of the type under consideration here may have a diameter of the order of magnitude of 2 to 3 cm.

While not being apparent from FIG. 1, there is disposed, interiorly in the muff section 2, inside its closed volume, a noise absorbent for passive damping of extraneous noise, the noise absorbent preferably consisting of foamed material displaying open foam structure. In the region between the loudspeaker element 4 and the user's ears, there is however an open area without damping material, so that direct sound from the loudspeaker element 4 may impinge on the user's ears, which gives optimum sound reproduction. However, it is also possible to dispose a minor amount of damping material, or a damping material displaying less damping, between the loudspeaker element 4 and the user's ear. The noise absorbent has also proved to have a favourable effect on the frequency path at approx. 2000 Hz, where a marked dip would otherwise occur.

The amount of damping material disposed in the muff section 2 and also the dimensioning of the muff section 2, i.e. the enclosed volume, may vary from one case to another, depending on which damping characteristic is intended for passive noise damping.

The loudspeaker element 4 has a membrane 5 which is drivable under the action of a magnet system 6 or other drive means, such as a piezoelectric drive means. In such instance, the membrane 5 will move in a direction from left to right in FIG. 1, i.e. towards and away from the user's ear. The side of the membrane 5 facing towards the user's ear may be considered as the front side of the membrane, while the opposing side of the membrane may be considered as its rear side. In order to prevent acoustic shorting of the loudspeaker element 4, the rear side of the membrane works towards a closed volume which is thus discrete and separate from the region in front of the front side of the membrane 5. This closed volume is defined on the one hand by the membrane and on the other hand by the enclosure. The enclosure may be a capsule 7 integrated in the loudspeaker 4, but may also be a separate unit or be wholly or partly integrated in the hearing protector, principally its muff section 2.

The embodiments of the loudspeaker element 4 shown on the Drawings are of a commercially available type. In this loudspeaker, both the membrane and the magnet system are mounted in a capsule 7, with a front wall 8 facing towards the user's ear, the wall being foraminated or perforated in order to permit sound generated by the membrane to reach the user's ear. The front wall 8 may also in certain embodiments be replaced by a more or less dense latticework or possibly by a sound permeable piece of protective material.

The rear (i.e. to the right in FIG. 1) located portion of the capsule 7 encloses an air volume which must be separate and discrete from the region immediately in front of the membrane 5 in order to avoid acoustic shorting of the loudspeaker element 4. Because of the small dimensions of the loudspeaker element 4 and the capsule, this enclosed air volume will be slight, which negatively affects the base reproduction.

According to the present invention, the capsule 7 has a circumferential, peripheral wall which interconnects the rear portion 13 of the capsule 7 with the front wall 8 and which has a circumferential groove 9. The muff section 2 has a rear wall 10 with a tubular collar 11 directed towards the user's ears, and having, at its free end, an inwardly directed, circumferential bead 12 which is accommodated in or snapped into the groove 9 of the capsule 7. The connection between the peripheral, circumferential wall of the capsule 7 and the collar 11 or the bead 12, respectively, is tight so that no air flow can take place between the interior of the muff section 2 and its ambient surroundings.

According to the present invention, the air volume enclosed behind the membrane 5 interiorly in the capsule 7 or in the above-mentioned enclosure is in flow communication with the surroundings outside the closed space of the muff section 2. This is realised in that there are provided, in the rear capsule wall 13 of the capsule or in the defining wall of the enclosure, one or more holes or apertures which discharge interiorly in the covering section 3, whose enclosed volume is in flow communication with the ambient surroundings outside the muff 1. Longer or shorter, tubular ducts or channels may also come into consideration here.

The number of holes in the rear capsule wall 13, as well as the size of each one of them may vary, but it should be observed that but a single small hole of a diameter of 0.3 mm does not affect the frequency path to such an extent that any difference will be clearly tangible on measurement. On the other hand, already a hole of a diameter of 0.5 mm plus a hole of diameter of 0.3 mm will make it possible to achieve a considerable increase of the level at low frequencies. This applies regardless of whether measurement is carried out on a muff with a slight volume or on a muff with a large volume (thus the volume enclosed in the muff section 2 separate and discrete from the ambient surroundings). See further Tables 1 and 2.

The difference in frequency path between a muff of large volume in relation to a muff with a small volume is quite small, but the base lift at the lowest frequencies is slightly smaller in the large muff. In both large and small muffs, a very large hole (diameter>2.5 mm) does not give much more base lift on the really low frequencies (20-40 Hz) than do three to four holes of a diameter of 0.5 mm. On the other hand, the lift in volume is greater in the frequency range from 50 to 300 Hz.

In the foregoing, it was mentioned that the number and size of the holes or the apertures affect the frequency path. After measurements and listening tests, it was established that excessively large, total hole areas A (mm$^2$) should be avoided, since the level increase then extends too far up in frequency, in order subsequently to give a dip in the range of immediately below 1000 Hz, i.e. in the lower part of the speech frequency range. In addition, the base predominates and damping deteriorates. An upper limit of approx. 5.5 mm$^2$ should not be exceeded. However, extremely good results have been attained at approx. 0.2 mm$^2$.

As was mentioned above, too small a hole will give no or excessively poor effect, where approx. 0.1 mm$^2$ is an absolute minimum but more appropriately not less than approx. 0.2 mm$^2$.

Listening tests have shown that most people included in a listening panel think that a "moderately large base lift" is achieved employing a hole of a diameter of 0.3 mm together with a hole with a diameter of 0.5 mm. This implies a total hole area A of approx. 0.27 mm$^2$.

With the above-disclosed limits for the total hole area, the conclusion will be, in loudspeakers of different sizes with diameters in the region between 20 and 30 mm, that the total hole area should be less than approx 2% of the membrane area, but preferably also less than approx. 1% thereof.

Figure 2:
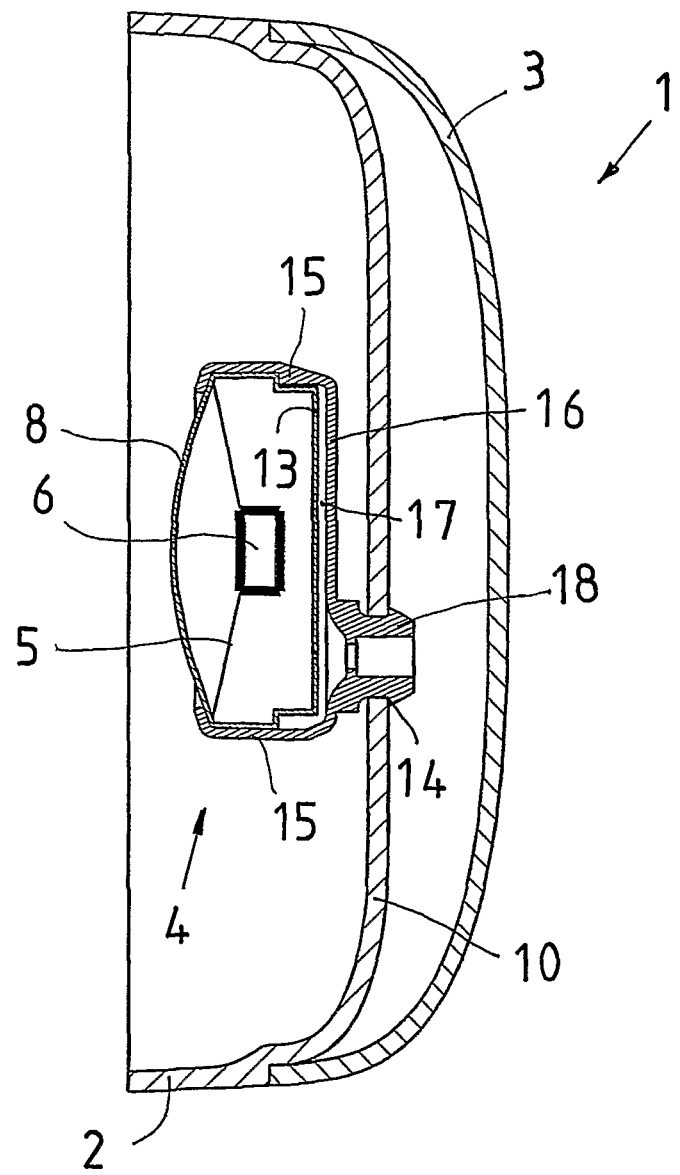
FIG. 2 shows a modified embodiment of the present invention.

FIG. 2 shows a slightly modified embodiment of the hearing protector according to the present invention. In this embodiment, the rear wall 10 of the muff section 2 has a smaller aperture 14, in which a retainer 15 of resilient, possibly elastic rube-like material is secured. The retainer 15 surrounds at least partly and seals against the outside of the capsule of the loudspeaker element 4. Also in this embodiment, the front wall 8 of the capsule is foraminated, perforated or otherwise open for the sound that is generated by the membrane 5 of the loudspeaker element 4.

As in the above-described embodiment, the capsule according to FIG. 2 has a rear capsule wall 13 which is located a distance from a corresponding rear wall 16 in the retainer 15 so that there is formed a cavity 17 between both of the walls in which the above-mentioned apertures, holes or ducts through the rear wall 13 of the cavity discharge. The cavity 17 is, via an aperture in the fixing portion 18 of the retainer 15, in flow communication with the interior of the covering section 3 which in turn is in flow communication with the ambient surroundings outside the closed space of the muff section 2. The above-mentioned aperture in the fixing portion 18 may, according to the present invention, also be employed to lead in those lines or conductors that are required for driving the magnet system 6 of the loudspeaker element.

TABLE 1

(Small muff)

| Measuring frequency (Hz) | Hole area + number (Ø mm) | | | | | | |
|---|---|---|---|---|---|---|---|
| | 0 | 1 × 0.3 | 1 × 0.5 + 1 × 0.3 | 2 × 0.5 + 1 × 0.3 | 3 × 0.5 + 1 × 0.3 | 4 × 0.5 + 1 × 0.3 | 1 × 2.5 + 4 × 0.5 + 1 × 0.3 |
| 30 | 56 | 57 | 67 | 68 | 70 | 71 | 72 |
| 60 | 57 | 57 | 63 | 65 | 68 | 71 | 72 |
| 100 | 57 | 57 | 60 | 62 | 65 | 66 | 70 |
| 200 | 58 | 58 | 58 | 58 | 60 | 62 | 66 |

TABLE 2

(Large muff)

| Measuring frequency (Hz) | Hole area + number (Ø mm) | | | | | | |
|---|---|---|---|---|---|---|---|
| | 0 | 1 × 0.3 | 1 × 0.5 + 1 × 0.3 | 2 × 0.5 + 1 × 0.3 | 3 × 0.5 + 1 × 0.3 | 4 × 0.5 + 1 × 0.3 | 1 × 2.5 + 4 × 0.5 + 1 × 0.3 |
| 30 | 54 | 54 | 64 | 67 | 68 | 69 | 70 |
| 60 | 55 | 55 | 60 | 65 | 67 | 68 | 71 |
| 100 | 55 | 55 | 57 | 51 | 64 | 66 | 72 |
| 200 | 56 | 56 | 56 | 57 | 58 | 60 | 68 |

What is claimed is:

1. A hearing protector with loudspeakers and comprising, a closed muff disposed at each ear of a user, the muff sealingly abutting against the user's head, whereby there is formed an enclosed space in the muff and around the user's ear, one loudspeaker disposed in at least one of the muffs and displaying a membrane whose one side is turned to face towards the ear of the user and whose opposing side is turned to face towards a closed volume which is defined by the membrane and an enclosure, and a drive unit for driving the loudspeaker, characterised in that the interior of the enclosure is, via at least one hole or duct in a defining wall of the enclosure, in communication with the ambient surroundings outside the closed space of the muff, wherein the total area of the hole/holes or duct/ducts lies in the range of $5.5 > A > 0.1$ mm$^2$.

2. The hearing protector as claimed in claim 1, characterised in that the enclosure comprises a capsule which is an integrated part of the loudspeaker.

3. The hearing protector as claimed in claim 1, characterised in that the enclosure is at least partly a part of the muff.

4. The hearing protector as claimed in claim 1, characterised in that there is disposed, interiorly in the closed space of the muff, a noise absorbent, and that, in the region between the loudspeaker and the user's ear, there is a region without noise absorbent or a region with a noise absorbent with lower damping.

5. The hearing protector as claimed in claim 1, characterised in that the area lies in the range of $0.5 > A > 0.1$ mm$^2$.

6. The hearing protector as claimed in claim 1, characterised in that the area is less than 2% of the membrane area of the loudspeaker, preferably less than 1% thereof.

7. The hearing protector as claimed claim 2, characterised in that the muff has an outer wall facing away from the user's ear, and having an aperture in which the capsule of the loudspeaker is sealingly accommodated.

8. The hearing protector as claimed in claim 7, characterised in that there is disposed around the aperture a collar extending towards the user's ear and having a radially inwardly directed bead along the free end, the bead being accommodated or snapped into a corresponding circumferential groove along the periphery of the capsule.

9. The hearing protector as claimed in claim 2, characterised in that the muff has an outer wall facing away from the user's ear, and having an aperture in which is sealingly inserted a fixing portion on a retainer in which the capsule of the loudspeaker is sealingly accommodated, there being disposed, interiorly in the retainer, a cavity in which the aperture or duct of the capsule discharges, and the cavity being in communication with the ambient surroundings outside the closed space of the muff by the intermediary of an aperture or duct in the fixing portion.

10. The hearing protector as claimed in claim 9, characterised in that the retainer consists of a resilient, possibly elastic rubber-like material.

11. The hearing protector as claimed in claim 9, characterised in that the retainer has a sleeve-shaped portion which surrounds and sealingly abuts against a peripheral, circumferential region of the capsule.

* * * * *